US007314457B2

(12) United States Patent
Reaux

(10) Patent No.: US 7,314,457 B2
(45) Date of Patent: Jan. 1, 2008

(54) ORTHOPEDIC CAST OR SPLINT

(76) Inventor: Brian K. Reaux, 710 Rock Hill Dr., Red Oak, TX (US) 75154

( * ) Notice: Subject to any disclaimer, the term of this patent is extended or adjusted under 35 U.S.C. 154(b) by 23 days.

(21) Appl. No.: 10/898,806

(22) Filed: Jul. 26, 2004

(65) Prior Publication Data
US 2005/0043664 A1  Feb. 24, 2005

Related U.S. Application Data

(63) Continuation-in-part of application No. 10/298,708, filed on Nov. 18, 2002, now abandoned.

(60) Provisional application No. 60/402,084, filed on Aug. 9, 2002, provisional application No. 60/400,515, filed on Aug. 2, 2002, provisional application No. 60/392,385, filed on Jun. 29, 2002.

(51) Int. Cl.
*A61F 5/00* (2006.01)

(52) U.S. Cl. .................. 602/6; 602/8; 602/61; 602/62; 602/63

(58) Field of Classification Search .................. 602/3, 602/8, 62, 63, 60, 901, 1, 14, 17, 18, 19, 602/20, 23, 5, 6, 9, 12, 61, 64, 21, 22; 128/879, 128/880, 877, 878; 2/16, 170, 161.1; D24/190
See application file for complete search history.

(56) References Cited

U.S. PATENT DOCUMENTS

| 482,095 | A | * | 9/1892 | McGlurg ..................... 66/187 |
|---|---|---|---|---|
| 1,245,253 | A | * | 11/1917 | Marglous ..................... 602/30 |
| 1,798,201 | A | * | 3/1931 | Hedges ........................... 2/239 |
| 1,999,929 | A | * | 4/1935 | Hearn ............................ 2/239 |
| 2,424,056 | A | * | 7/1947 | Ruth ............................. 2/241 |
| 3,302,642 | A |   | 2/1967 | Allen |
| 3,307,537 | A | * | 3/1967 | Simon et al. ................... 602/8 |
| 3,421,501 | A |   | 1/1969 | Beightol |
| 3,421,761 | A | * | 1/1969 | Grant ........................... 473/61 |
| 3,656,475 | A |   | 4/1972 | Hanrahan, Jr. |
| 3,656,476 | A |   | 4/1972 | Swinney |
| 3,881,473 | A |   | 5/1975 | Corvi et al. |
| 4,105,025 | A |   | 8/1978 | Wang et al. |
| 4,131,114 | A |   | 12/1978 | Kirkpatrick et al. |
| 4,134,397 | A |   | 1/1979 | Gianakakos |
| D259,955 | S | * | 7/1981 | Helferich .................... D24/190 |
| 4,407,499 | A | * | 10/1983 | Newton ........................ 473/61 |
| 4,502,479 | A |   | 3/1985 | Garwood |
| 4,709,694 | A | * | 12/1987 | O'Connell .................... 602/21 |
| D294,736 | S | * | 3/1988 | Thygesen .................. D24/189 |

(Continued)

OTHER PUBLICATIONS

Royce Medical, Techform Product Brochure, pp. 1-2, No Date.

(Continued)

*Primary Examiner*—Kim M. Lewis
(74) *Attorney, Agent, or Firm*—Grady K. Bergen; Griggs Bergen LLP

(57) ABSTRACT

An orthopedic stockinette includes a preformed sleeve of elastic fabric material. At least a portion of the sleeve is drawn together to form secondary sleeves for receiving digits of a wearer and serving as a divider between the received digits. An orthopedic cast or splint may be formed with the stockinette by providing a layer of overlaying layer of hardenable cast material.

20 Claims, 3 Drawing Sheets

U.S. PATENT DOCUMENTS

| | | | |
|---|---|---|---|
| 4,888,225 | A | 12/1989 | Sandvig et al. |
| 4,964,824 | A * | 10/1990 | Spencer et al. .............. 441/57 |
| 5,016,622 | A | 5/1991 | Norvell |
| 5,054,129 | A * | 10/1991 | Baehr ........................... 2/409 |
| 5,228,164 | A | 7/1993 | Graf |
| 5,415,622 | A * | 5/1995 | Kelley ........................... 602/5 |
| 5,623,734 | A * | 4/1997 | Pugliatti ....................... 2/239 |
| 5,833,637 | A * | 11/1998 | Pong .............................. 602/5 |
| 5,867,838 | A * | 2/1999 | Corry ........................... 2/239 |
| 5,968,536 | A * | 10/1999 | Godfrey ..................... 424/402 |
| 6,010,473 | A * | 1/2000 | Robinson ..................... 602/21 |
| 6,093,161 | A | 7/2000 | Vlaeyen et al. |
| 6,093,163 | A * | 7/2000 | Chong et al. ................ 602/30 |
| 6,200,286 | B1 | 3/2001 | Zamani |
| 6,334,222 | B1 * | 1/2002 | Sun ............................... 2/239 |
| 6,334,854 | B1 * | 1/2002 | Davis ........................... 602/6 |
| 6,405,381 | B1 * | 6/2002 | Bowman, Jr. ................. 2/170 |
| 6,443,919 | B1 * | 9/2002 | Castro ......................... 602/27 |
| 6,585,671 | B2 | 7/2003 | Rhee |
| 6,808,501 | B2 * | 10/2004 | Stess et al. ................... 602/6 |
| D498,916 | S * | 11/2004 | Lowell ....................... D2/980 |
| D503,529 | S * | 4/2005 | Russell ...................... D2/980 |
| 6,953,441 | B2 * | 10/2005 | Goumas ....................... 602/7 |
| 2004/0186402 | A1 * | 9/2004 | Bennett ....................... 602/21 |

OTHER PUBLICATIONS

Deroyal, Product Information Sheet, pp. H-1 to H-9, No Date.
RX Textiles, Lower Extremity Orthotics Sock Product Information, No Date.
RX Textiles, Upper Extremity Orthotics Sock Product Information Sheet, No Date.
DePuy Orthopaedics, Inc., Below Knee Cast FRC Technique Guidelines, pp. 1-2, 2001.
DePuy Orthopaedics, Inc., Volar Forearm Cast FRC Technique Guidelines, pp. 1-2, 2001.
DePuy Orthopaedics, Inc., Above Knee Cylinder FRC Technique Guidelines, pp. 1-2, 2001.
M-Pact Cast Room Supplies Product Information Sheet, pp. 1-2, No Date.
DePuy Orthopaedics, Inc., Thumb Cast FRC Technique Guidelines, pp. 1-2, 2001.
DePuy Orthopaedics, Inc., Tibial Gaiter FRC Technique Guidelines, pp. 1-2, 2001.
Deroyal, Stockinette Product Information Sheet, pp. D-16 to D-17, No Date.
DePuy Orthopaedics, Inc., Forearm Cast FRC Technique Guidelines, pp. 1-2, 2001.
DePuy Orthopaedics, Inc., Hallux Cast FRC Technique Guidelines, pp. 1-2, 2001.
DePuy Orthopaedics, Inc., Ankle Stirrup FRC Technique Guidelines, pp. 1-2, 2001.
Johnson & Johnson, Delta-Lite, Delta-Cast, FlashCast Instructions for Use, pp. 1-3, 1998.
3M Scotchcast Casting Products Information Sheet, pp. 1-3, 1998.
Rockwood, et al., Fractures in Children vol. 3, 1984, pp. 231, 239, 242-243, 262.
Rockwood, et al., Fractures in Children vol. 3, 1984, pp. 1438-1439.
Salter, Textbook of Disorders and Injuries of the Musculoskeletal System. 1999, pp. 564.
Green, D.P., Operative Hand Surgery, 3rd. Ed., 1993, pp. 701, 739.

* cited by examiner

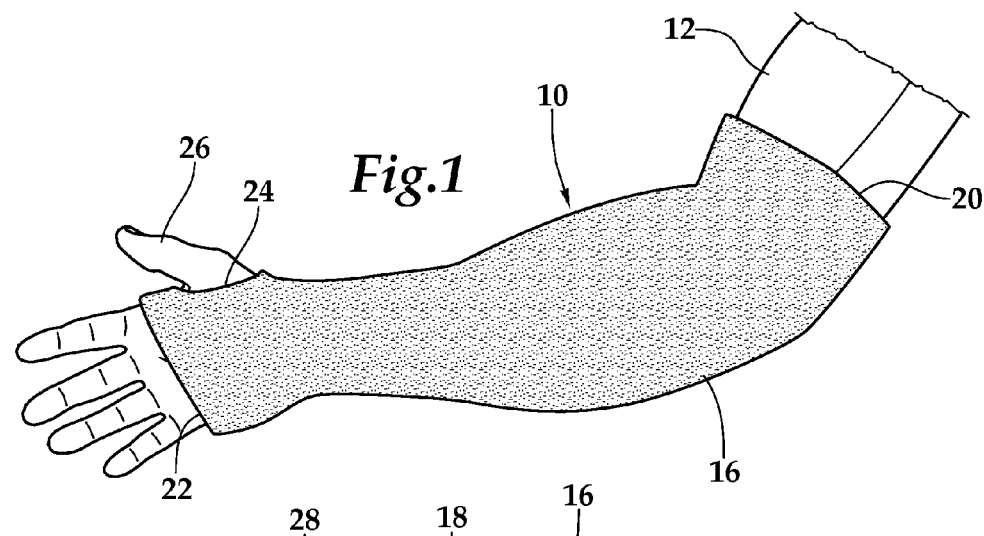
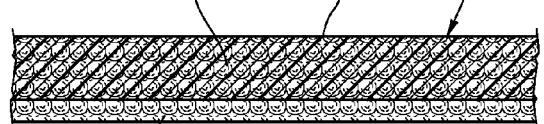
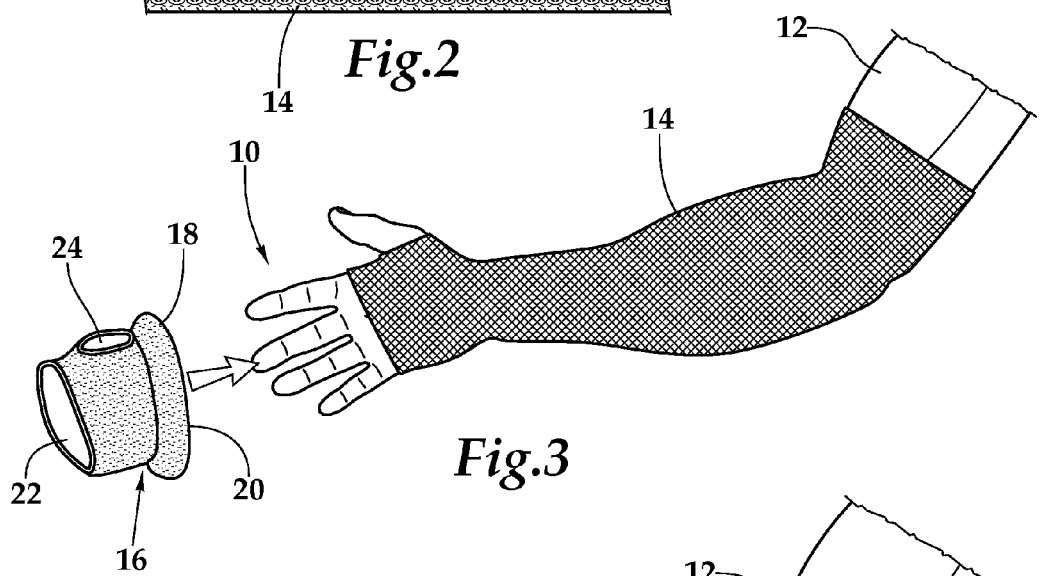
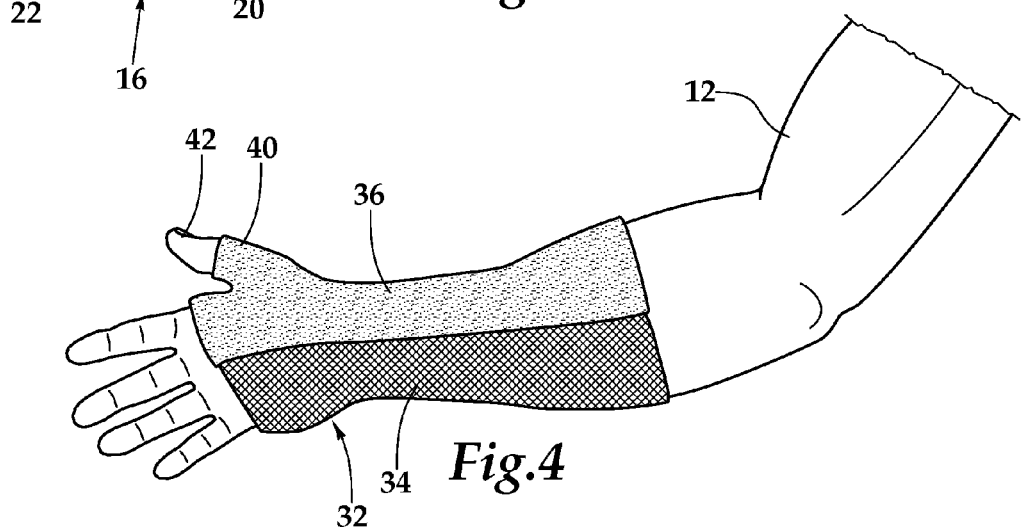

… (1)

ORTHOPEDIC CAST OR SPLINT

This application is a continuation-in-part of U.S. patent application Ser. No. 10/298,708, filed Nov. 18, 2002, now abandoned, and entitled "Orthopedic Cast or Splint," which claims the benefit of U.S. Provisional Patent Application Nos. 60/392,385, filed Jun. 29, 2002; 60/400,515, filed Aug. 2, 2002; and 60/402,084, filed Aug. 9, 2002.

TECHNICAL FIELD

The invention relates generally to orthotics.

BACKGROUND

Conventional orthopedic casts are typically formed from long tapes or bandages of gauze material that have been impregnated with a plaster material. The lengths of plaster impregnated gauze ate usually provided on rolls that may be dipped in water to activate the plaster, unrolled and wrapped around an affected body part or limb to form a cast shell. Forming the cast is usually a very time consuming and involved process. This typically involves first positioning a liner or stockinette over the area to be covered by the impregnated gauze material. Padding material, such as cotton, may be positioned over the liner prior to application of the impregnated gauze. The padding material serves as a spacing element to facilitate removal of the cast shell. Forming the shell of the cast is achieved by winding the lengths of impregnated tape circumferentially around the limb or body part. The tape or gauze is gradually layered and overlapped until the desired area of coverage and shell thickness is achieved. The winding of the impregnated gauze may be an intricate process, particular when forming spicas or where intricate tape crossings are necessary.

While conventional casts have been used for many years, they have many disadvantages and shortcomings. As already discussed, forming the cast is a time consuming, highly involved and intricate process. Conventional casts are usually heavy, bulky and cumbersome to wear. The padding underlying the shell is prone to absorbing and retaining moisture so that care must be used to prevent the cast from getting wet. The casts often lack X-ray transparency, making removal of the cast necessary for X-ray photography and monitoring of healing progress. Removal of the cast can be difficult, requiring the need for saws or specialized cast cutting equipment. Additionally, the padding material must be included as an element of the cast to protect the user from injury during sawing and removal. Sawing also creates undesirable dust and debris.

BRIEF DESCRIPTION OF THE DRAWINGS

For a more complete understanding of the present invention, and the advantages thereof, reference is now made to the following descriptions taken in conjunction with the accompanying figures, in which:

FIG. 1 illustrates a cast for an arm constructed in accordance with the invention;

FIG. 2 is a cross-sectional view of a portion of the cast of FIG. 1;

FIG. 3 is a perspective view of an impregnated sleeve of the cast of FIG. 1, shown as the sleeve is positioned on the arm of a wearer;

FIG. 4 shows a thumb "spica" splint constructed in accordance with the invention;

DETAILED DESCRIPTION

Figure 5:
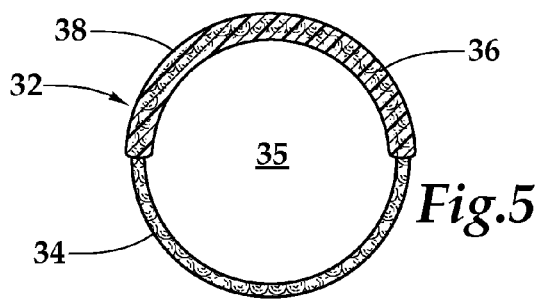
FIG. 5 is a cross-sectional view of the splint of FIG. 4.

Referring to FIG. 1, an orthopedic long arm cast 10 is shown. Although the cast 10 is shown as being that for an arm and wrist 12 of an adult human, casts or splints as described herein may be used for other body parts, as well. As used herein, unless otherwise stated, the term "human" may encompass adults, children, infants, newborns, etc. without limitation to age or size. Additionally, the casts or splints may be used for animals of any age or size for which the utilization of a cast or splint would be useful or appropriate. The cast or splint may be used for treatment of fractures or sprains to limit movement or immobilize a limb, joint, bone or other body part or portion of the anatomy.

The cast 10 may be formed with a liner or stockinette 14 (FIG. 2) layer that underlies a cast shell layer 16 and which may form a part of the final cast. The liner or stockinette 14 may be a thin, lightweight fabric or other material, and may the same or similar to those commonly used in the construction of conventional casts. The liner or stockinettes may be of natural or synthetic material or a blend of such materials. The liner may be formed as a tubular sleeve with at least one end opening and that defines a circumferentially enclosed passage that is prefabricated to generally fit and conform to the appropriate body part for which it is to be used, including appropriate openings or secondary sleeves for the passage of the body part and any projecting members or appendages thereof, such as fingers, toes, etc. An example of a suitable stockinette material is cotton or a blend of cotton and a synthetic material.

An elastic material, such as Lycra® synthetic fibers or material, may be incorporated into the liner or stockinette so that it expands and contracts to facilitate placement of the stockinette on the limb or body part and to provide a conforming fit. In certain cases, the liner or stockinette may be treated with or have incorporated therewith an antimicrobial compound or agent. Additionally, the liner or stockinette may be fluid repellent or breathable, allowing the passage of water vapor but repelling penetration by water or other liquids to keep the underlying skin as dry as possible.

The cast shell 16 is formed from a preformed or prefabricated sleeve of flexible material 18. As used herein, the terms "preformed" or "prefabricated" are meant to encompass the feature of the stockinette or sleeve being formed or fabricated prior to positioning on the body part or limb for which it is used without substantial modification. The material 18 used for the shell 16 may be formed from fabric material such that formed from natural fibers (such as cotton, linen, etc.), mineral fibers (such as fiberglass, etc.), or synthetic fibers (such as polyester, polypropylene, polyamide, etc.) or combination of these, and which may be formed into one or more layers of woven or non-woven fabric.

The fabric 18 may include an elastic material, such as Lycra®, polyurethane, rubber or other elastomers, to facilitate expansion and contraction of the material during placement or positioning of sleeve over the limb or body part and to provide a conforming fit. Other characteristics of the fabric material may be the same or similar to those described in U.S. Pat. No. 5,228,164, which is directed toward the formation of lasts or molds for footwear, and which is herein incorporated by reference for all purposes. The fabric material of the sleeve 18 should be of sufficient thickness to provide the necessary orthopedic supporting function when combined or provided with the impregnated hardenable material, as is discussed below. Thicknesses may vary, but examples of suitable thicknesses for the fabric material may be from about 3 mm, 5 mm, 6 mm, 8 mm, 10 mm, 12 mm or more. An example of a commercially available material for the fabric sleeve includes the fabric material available as Tubular Terry Net™, from RX Textiles, Charlotte, N.C.

The material 18 may also be a non-fabric material, such as a flexible foam, that is capable of performing in a similar manner to the fabric as is described herein and will be appreciated by those skilled in the art.

The sleeve 18 may be of generally continuous or unitary construction in that it is formed as a single unit prior to positioning on the body part or limb. It should be apparent to those skilled in the art that although the sleeve 18 is described as being of continuous or unitary construction, it may be formed from one or from two or more sections or pieces of material that are joined or coupled together, such as by sewing, knitting, fusing, adhesion or otherwise, to form such construction, and is not necessarily meant to limit the construction as being formed from only a single component or piece of material. The sleeve 18 may be generally tubular in shape with at least one end opening 20 and that defines a circumferentially enclosed central passage for receiving the body part upon which it is positioned. The sleeve 18 may be open at both ends, such as at the end 22 (FIG. 2) to allow the passage of the limb or body part therethrough. One or more secondary openings, such as the opening 24, may also be formed within the wall of the sleeve 18 to allow the passage and projection of a projecting member, such as the wearer's thumb 26. The opening 22 and the secondary openings may be preformed or may be formed, such as by cutting, during construction of the cast when positioning the sleeve on the body of the wearer. It may be desirable, however, to provide such openings as part of the prefabricated sleeve so that no cutting or modification is necessary during cast construction.

The fabric sleeve 18 of the cast 10 is circumferentially impregnated with a hardenable material 28 (FIG. 2). The hardenable material 28 may cover substantially the entire sleeve 18, extending circumferentially around and substantially along the entire length of the sleeve 18. The hardenable material 28 may add a slight amount of thickness to the fabric sleeve 18 when coated thereon. This may be one or two millimeters or more of additional thickness. The hardenable material 28 may be a plaster, resin, polymer or other suitable material that can be applied to the fabric material of the sleeve and that is initially pliable and does not substantially interfere with the flexibility of the fabric material of the sleeve 18 prior to hardening. This facilitates positioning and conformance of the sleeve 18 on the affected limb or body part to be supported. The hardenable material may also harden or cure upon activation to a sufficient hardness or rigidity to provide a supporting function within a matter of few minutes to one or two hours or more. The hardenable material may include water-curable, air-curable, heat-curable, U.V.-curable, etc. type plasters or resin materials. Examples of hardenable materials, as well as certain fabric materials, are disclosed in U.S. Pat. Nos. 3,656,476; 3,881,473; 4,105,025; 4,131,114; 4,502,479; 4,609,578; 4,655,208; 4,667,661; 4,668,563; 4,705,840; 4,774,937; 4,871,845; 4,888,225; 4,968,542 and 5,228,164, which are each herein incorporated by reference. An example of a suitable commercially available hardenable material is that available as Carapace™/DeRoyal (Product No. 01-10-9910) Natural Polymer, from DeRoyal Industries, Inc., Powell, Tenn.

The sleeve 16 may prefabricated to include a colorant or colorants to provide one or more colors to enhance the sleeve's appearance or attractiveness. An example of applying colorants to such materials is described in U.S. Pat. No. 5,088,484, which is herein incorporated by reference. Additionally, logos, symbols, illustrations, pictures or other visible enhancements wherein less than all or a portion of the sleeve is provided with different colors, variation of color or contrasting areas may be formed on or incorporated into the sleeve 16 to enhance its appearance.

In construction of the cast 10, as shown in FIG. 3, the stockinette 14 is first positioned over the arm, wrist and hand 12, as shown. The preimpregnated sleeve 16 may be initially provided in a sealed or moisture-proof container (not shown), such as a disposable envelope or pouch, that is opened prior to application. Condoms or other temporary protective coverings (not shown) may be positioned on the fingers or appendages that are to be exposed, such as the thumb 26, during construction of the cast. The sleeve 16 may be in a rolled or substantially rolled or folded configuration to facilitate positioning of the sleeve 16 on a limb or body part. If necessary, the impregnated sleeve 16 may be dipped in or sprayed with water (for water-curable type resins or plasters) or otherwise activated prior to positioning on the wearer. Alternatively, the impregnated sleeve may be activated after it has been positioned on the wearer.

In the embodiment shown, the rolled sleeve 16 is positioned on the wearer's arm 12 by directing the hand and arm through the opening 20. The sleeve 16 is preformed with the opening 22 provided for the fingers of the wearer's hand and the secondary opening 24 provided for the wearer's thumb. The sleeve 16 may be activated by dipping in water, if the hardenable material is a water-curable material, prior to unrolling, if desired. As the wearer's hand and arm are inserted through the sleeve 16, the sleeve 16 may be gradually unrolled or unfolded generally longitudinally along the length of the wearer's hand and arm until the sleeve is substantially unrolled. This may be done without any circumferential wrapping or overlapping of fabric material, as occurs with conventional gauze-tape-type casts. If necessary, the sleeve may be rotated, molded, reduced, smoothed or adjusted to provide the necessary conformance and fit for the wearer and to align the fracture or properly support the limb or body part. Additionally, if necessary, any excess material of the sleeve 16 may be trimmed after the sleeve 16 is unrolled to provide an appropriate fit.

After the sleeve 16 has been properly positioned on the wearer's arm 12, the sleeve 16 is allowed to cure or harden to provide the necessary rigidity and support for substantially immobilizing the wearer's arm and/or hand. The underlying stockinette 14 or portions thereof may become laminated to the sleeve 16 when it is positioned thereon so that it becomes an integral part of the cast 10. After the impregnated sleeve 16 has hardened, any condoms or protective coverings used in protecting the exposed fingers or appendages may be removed.

Although not shown, padding material, such as cotton, or other material, as is used in conventional casts, may also be positioned on the limb or body part prior to positioning of the sleeve. Such padding material may not be necessary, however. Because the shell of the cast 10 is relatively thin, it may be removed by cutting with a scissors or similar devices, making the use of conventional cast saw equipment unnecessary and eliminating the need for conventional cast padding. Also, casts or splints constructed in accordance with the invention may have sufficient transparency to X-rays so that the clear visibility of X-ray images of bone or bone fracture patterns is not less than, 85%, 90% or 95% by area.

Referring to FIG. 4, a thumb "spica" splint 32 is shown. As used herein and unless otherwise stated or as may be apparent from the context, the term "spica" is not to be construed to mean a spica formed as in conventional casts or splints wherein successive wraps of tapes or bandages are used to encase or surround a projecting member, but is merely used for ease of description and understanding to similarly correspond to a spica formed in such conventional casts or splints. The splint 32 may be similar in construction to the cast 10, employing generally the same or similar materials, as previously described. As seen in FIG. 5, the splint 32 is formed from a tubular fabric main sleeve 34 having a central opening 35. A shell portion 36 is formed on the sleeve 34 from a non-continuous or non-circumferential coating of hardenable material 38 that extends generally along one side of the sleeve 34 along its length. A thumb-spica portion 40 is also formed on the shell portion 36 from a secondary fabric sleeve that is integral with and preformed with the main sleeve portion 34 for receiving a wearer's thumb 42, and which is also impregnated with the hardenable material 38.

The hardenable material 38 may be impregnated on such non-continuous or selected portions by initially positioning the fabric sleeve on a mandrel or other device having a configuration or shape, which may be similar to the body part to which it is to be applied, that facilitates the application of the hardenable material to the fabric material of the sleeve. In this way, only selected portions of the fabric material may have the hardenable material applied thereon. The impregnated sleeve may then be removed from the mandrel, such as by longitudinal rolling or folding, wherein the impregnated sleeve will have a rolled or folded configuration, such as shown in FIG. 3 with respect to the sleeve 18 for the cast 10. For casts, circumferential portions or the entire or substantially the entire sleeve may be coated in the same way and removed from the mandrel in the rolled configuration, as well.

The splint 32 may be positioned and applied to the hand and arm in a manner similar to the cast 10, employing an underlying stockinette or liner and any necessary padding for protecting bony prominents.

Figure 6:
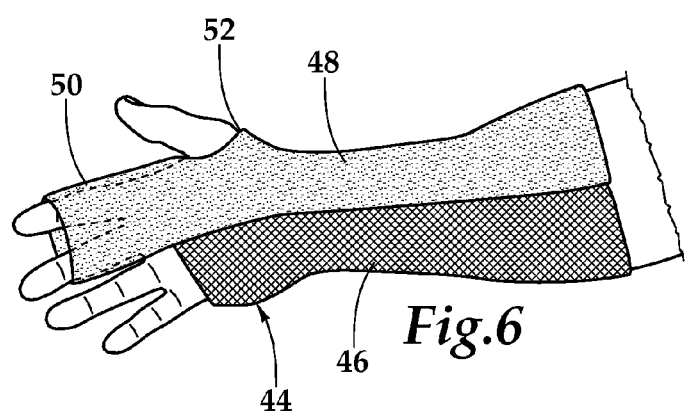
FIG. 6 shows a radial gutter splint constructed in accordance with the invention.

The casts or splints formed as generally described can have a wide variety of different configurations and applications. Referring to FIG. 6, a radial gutter splint 44 with encased $2^{nd}$ and $3^{rd}$ fingers of the wearer's hand is shown. The splint 44 includes a preformed fabric sleeve 46 having a non-circumferential impregnated portion 48 to form a non-circumferential shell that extends along the length of the wearer's forearm and has an integral finger shell spica portion 50 encasing the $2^{nd}$ and $3^{rd}$ fingers of the wearer's hand, and is provided with a secondary thumb opening 52.

Figure 7:
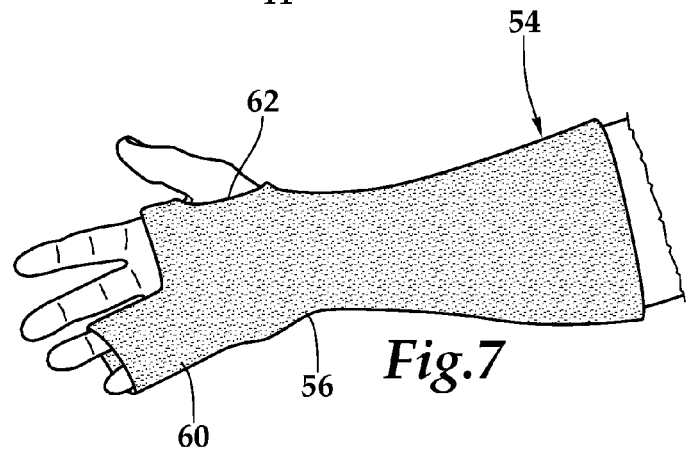
FIG. 7 shows an ulna gutter cast constructed in accordance with the invention.

FIG. 7 shows an ulna gutter cast 54 formed from a preformed fabric sleeve 56, which is circumferentially impregnated with a hardenable material, having a finger spica shell portion 60 encasing the $4^{th}$ and $5^{th}$ fingers, and a thumb opening 62.

Fabric sleeves similar to those previously described may also be impregnated with a hardenable material in a manner to form casts or splints of different configurations for use on the same or other body parts or limbs, such as hip spicas, and wherein the shell extends circumferentially or non-circumferentially or on less than all or only a portion of the sleeve. Examples of different casts or splints may include but are not limited to those for the hand, wrist, arm, leg, foot, ankle, spine, etc. Specific casts include, but are not limited to, radial gutter casts, ulna gutter casts, thumb spica casts, short arm casts, munster casts, long arm casts, long arm cylinder casts, long leg casts, long leg cylinder casts, short leg casts, delbet casts, patella tendon weight bearing casts, body jacket casts, single hip spica casts, double hip spica casts, minerva jacket casts, velpeau casts, shoulder spica casts, short leg splints, long leg splints, short arm splints, long arm splints, volar splints, sugar tong splints, radial gutter splints and thumb spica splints.

Figure 8:
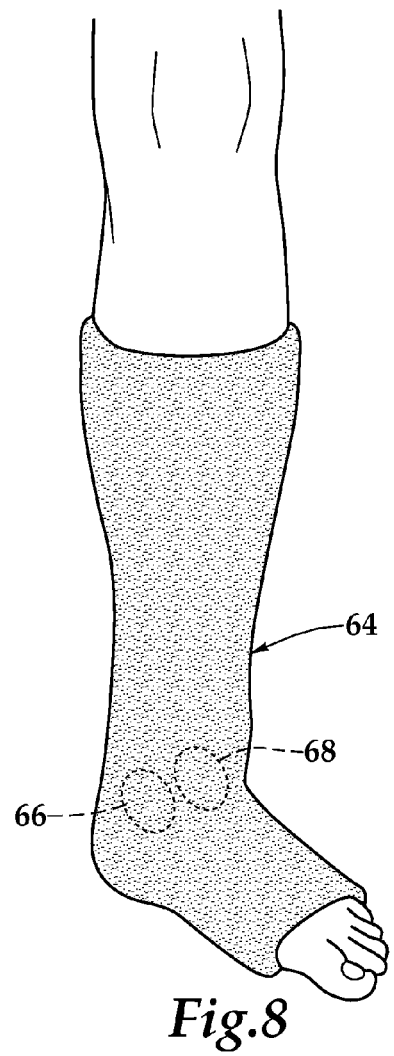
FIG. 8 shows a leg cast constructed in accordance with the invention.

FIG. 8 shows a leg cast 64 formed in a similar manner to the casts and splints previously described. The cast 64 also includes inner layers of padding material 66, 68 for overlaying bony prominent areas. The padding material may be felt, fabric, foam, or other suitable protective material that can be used to overlay bony prominents or other areas that may be susceptible to rubbing or increased pressure from the cast. The padding material may be secured to the outer surface or side of the underlying stockinette or liner, or may be secured to the inner surface or side of the impregnated sleeve such as by sewing, fusing, adhesion or otherwise.

The invention provides a lightweight, low-profile, non-bulky immobilizing support for a limb or other body part that can be quickly and easily constructed. The cast or splint can be provided at low cost and with less material than conventional casts or splints to achieve the required strength and support. The cast has high transparency to X-rays and can be easily removed without the need for cast saws or other specialized equipment, which can create debris and risk of injury to the cast wearer. The cast also eliminates the need for padding material, which is prone to absorbing and retaining moisture.

The following example serves to further illustrate the invention.

EXAMPLE

A test was conducted on an adult human male having a broken metacarpal of the right hand that had originally been fitted with a conventional splint to await the abatement of any swelling. The splint was removed in a conventional manner and a liner stockinette of Tubular Terry Net™, from RX Textiles, was positioned over the patient's hand and arm. The liner stockinette was provided with openings for the projection of the patient's thumb, as well as a separate opening for the $2^{nd}$ and $3^{rd}$ fingers. Next, a layer of padding material was placed over the liner and over the bony prominents of the patient's hand. The patient was provided with finger condoms to cover the exposed thumb and $2^{nd}$ and $3^{rd}$ fingers during construction of the cast.

Figure 9:
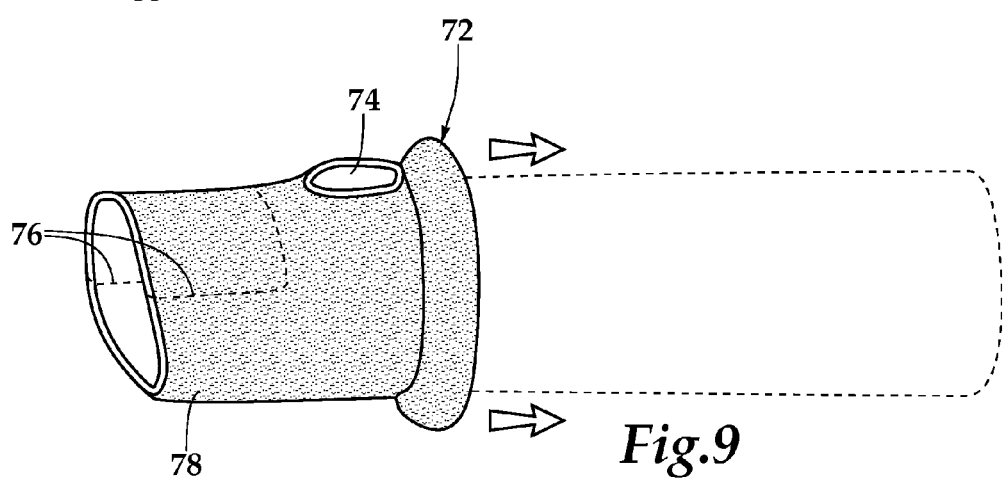
FIG. 9 shows the construction of a ulna gutter cast in accordance with the invention.

A preimpregnated 13" tubular, polyester sock was used for the cast shell 72 (FIG. 9). The sock had been impregnated with approximately 80 to 90 grams of a water-curable hardenable material, available as Carapace™ /DeRoyal (Product No. 01-10-9910) Natural Polymer, from DeRoyal Industries, Inc., Powell, Tenn., and rolled or folded longitudinally as shown in solid line. The sock for the shell had been precut to form a hole or opening 74 for the thumb for use as a shortarm cast, but was further modified to form an ulna gutter cast. This was done by cutting a portion, as outlined in dashed line at 76 of FIG. 9, of the sock approximately one inch above the thumb opening 74, leaving a remaining portion 78.

Prior to positioning on the patient's arm, the impregnated sock was dipped in tepid water to activate curing of the hardenable material. The impregnated sock was then positioned on the patient's right hand and arm by rolling the sock generally longitudinally along the length of the patient's hand and arm and over the liner and padding material while the sock was still in a flexible state, the thumb being received through the thumb opening 74 and the $2^{nd}$ and $3^{rd}$ fingers projecting through the opening formed by the removal of the portion 76. The remaining portion 78 of the sleeve was wrapped around the patient's $4^{th}$ and $5^{th}$ fingers and secured with conventional medical tape to form a spica. The sock was then smoothed and conformed to the patient's hand and arm to ensure that they were held in the proper position.

After allowing the cast to harden for a few minutes, the patient's right hand with the hardened cast was X-rayed. The resulting X-ray images clearly showed 100% of the bone and the fracture pattern.

After an elapsed period of approximately two weeks, the patient's right hand was examined and X-rayed again with the cast still in place. The X-ray images clearly showed the bone, the fracture pattern and a small amount of new bone growth. It was apparent that the cast was holding the fractured bone in place with no noticeable problems.

After another elapsed period of approximately two weeks, the cast was manually removed by cutting the cast with medical bandage scissors. The patient's arm and hand were visually examined and showed no apparent blisters, rashes, pressure sores, drainage or other tissue damage. During the period the patient was wearing the cast, the patient reported they were able to function in a generally normal manner and that the cast had gotten wet during bathing with no negative effects to the cast or skin.

Figure 10:
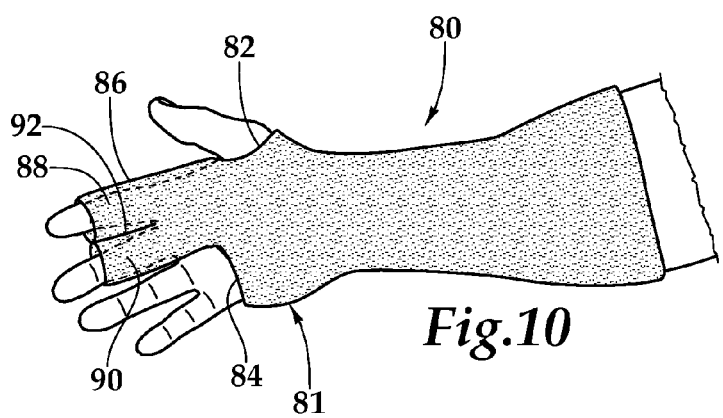
FIG. 10 shows a radial gutter stockinette liner for a cast positioned over the wrist and hand of a wearer and constructed in accordance with the invention.

Referring now to FIG. 10, a stockinette or liner 80 is shown for use in constructing a cast from the preformed sleeve, as described above, or for use in constructing a cast using conventional orthopedic cast wrapping techniques. The liner 80 may be formed from an elastic fabric material. Examples of suitable materials include those commercially available as Tubular Terry Net™, from RX Textiles, Charlotte, N.C. or Delta Terry-Net™, from DePuy Orthopaedics, Inc., Raynham, Mass. The material forming the liner 80 may have a thickness of from about 3 mm, 5 mm, 6 mm, 8 mm, 10 mm, 12 mm or more.

In the embodiment shown in FIG. 10, the liner 80 is a prefabricated liner configured for use in forming a radial gutter cast or splint. The liner 80 is formed as a tubular sleeve 81 that is open at one end for positioning the sleeve 81 over the wearer's hand and arm. A side opening 82 is provided for receiving the wearer's thumb. An opening 84 is provided for closely receiving the wearer's exposed $4^{th}$ and $5^{th}$ fingers, which pass therethrough. A finger sleeve 86 is provided for receiving the wearer's $2^{nd}$ and $3^{rd}$ fingers. The sleeve 86 extends beyond the opening 84 and may be of sufficient length to extend substantially along the entire length of the wearer's $2^{nd}$ and $3^{rd}$ fingers. The sleeve 86 is divided into individual compartments 88, 90 for receiving each of the $2^{nd}$ and $3^{rd}$ fingers, respectively. The compartments 88, 90 may be formed by drawing the material forming the sleeve 86 together, such as by stitching, along a longitudinal line 92, which forms a divider between the $2^{nd}$ and $3^{rd}$ fingers. Alternatively, individual sleeve compartments 88, 90 may be formed from separate pieces or sections of material.

The fabric material forming the sleeve 86 is of sufficient thickness to provide padding between the $2^{nd}$ and $3^{rd}$ fingers, without requiring cotton or other additional padding therebetween. In this way, contact between the fingers is prevented in areas that are enclosed by the cast.

The edges of openings and/or ends of the sleeve 81 may be provided with a hem or selvage to prevent unraveling of the woven or knitted material forming the sleeve 81.

In use, the stockinette 80 is positioned over the wearer's hand and arm with the wearer's thumb projecting out of opening 82 and with the $2^{nd}$ and $3^{rd}$ fingers being received in the sleeves 88, 90, respectively. The wearer's $4^{th}$ and $5^{th}$ fingers project and extend through opening 84. A layer of hardenable material may then be applied over the stockinette 80, such as with the impregnated cast sleeve described previously or with conventional wrapping techniques to form a cast or splint.

Figure 11:
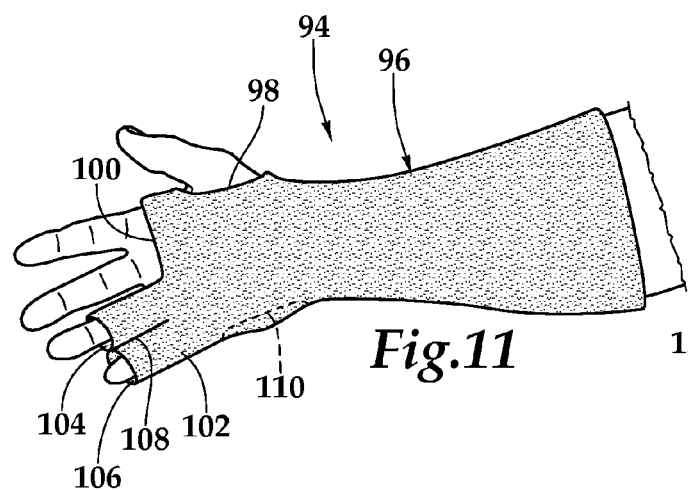
FIG. 11 shows a ulna gutter stockinette liner constructed in accordance with the invention.

FIG. 11 shows a similar stockinette or liner 94 for use in forming an ulna gutter cast or splint. The stockinette 94 is preformed from a sleeve 96 of elastic fabric material, which may be the same or similar to the material of liner 80. The liner 96 is open at one end for positioning the sleeve 96 over the wearer's hand and arm. A side opening 98 is provided for receiving the wearer's thumb.

An opening 100 is provided for receiving the wearer's exposed $2^{nd}$ and $3^{rd}$ fingers, which pass and extend therethrough. A finger sleeve 102 is provided for receiving the wearer's $4^{th}$ and $5^{th}$ fingers. The sleeve 102 extends beyond the opening 100 and may be of sufficient length to extend substantially along the entire length of the wearer's $4^{th}$ and $5^{th}$ fingers. The sleeve 102 is divided into individual compartments 104, 106 for receiving each of the $4^{th}$ and $5^{th}$ fingers, respectively. The compartments 104, 106 may be formed by drawing the material forming the sleeve 102 together, such as by stitching, along a longitudinal line 108, which forms a divider between the fingers.

It should be noted that an optional second side opening 110 may be provided in the sleeve 96 opposite the opening 98 so that the stockinette 94 can be alternatively used as a liner for a radial gutter cast or splint, similar to the liner 80. Alternatively, the openings 98 or 110 may be cut or made in the sleeve 96 by the technician or one forming the cast at the time the cast is being formed.

Figure 12:
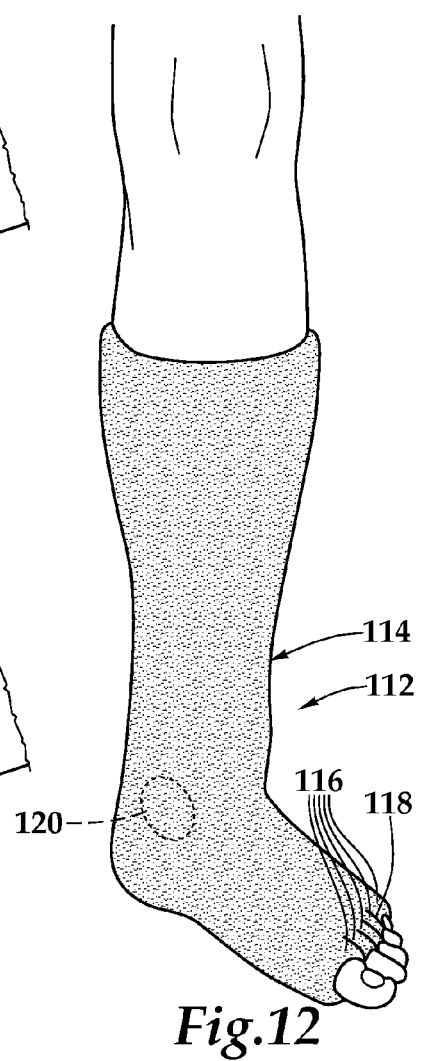
FIG. 12 is a stockinette liner for a foot constructed in accordance with the invention.

Referring to FIG. 12, a stockinette 112 for use on the foot is shown. The stockinette 112 is formed from an elastic fabric sleeve 114, which may be the same or similar to the material of the stockinettes 80 and/or 94. The sleeve 114 is open at one end and terminates at the other end in a one or more toe sleeves or compartments 116. In the embodiment shown, five toe sleeves 116 are provided. The toe sleeves 116 are formed by drawing the material of the sleeve 114 together along longitudinal lines 118, which may be formed by stitching or otherwise permanently drawing the material of the sleeve 116 together along the lines 118. The ends of each of the toe sleeves 116 may be open at the ends to allow visual inspection of capillary refill of the toes during formation of the cast. Alternatively, the sleeves 116 may be closed at the ends. An additional layer of padding material 120 may also be coupled to the sleeve 114 to facilitate cushioning of bony prominent areas.

The stockinettes described may be preformed or partially preformed with the secondary sleeves and packaged in a suitable manner with indicia to indicate their end use or type of cast or splint. This may include indication of one of a radial gutter cast, ulna gutter cast, foot, etc.

The preformed stockinettes for the hands and feet as described above are a significant improvement over the prior art. The stockinette provides a divider and cushion between the fingers, toes or other digits without the need for additional padding materials or wrappings. The prior art method of positioning and securing layers of cotton or other padding material between adjacent finger, toes or digits that underlay the hardened cast material is a time consuming and involved process.

With the preformed stockinettes of the invention, the stockinette is merely positioned over wearer's hand or foot, with the finger or toe sleeves separating and cushioning the wearer's fingers or toes. This prevents skin maceration or webbing that may occur if there is skin to skin contact between the fingers or toes. The finger or toe sleeves may also act as coverings or warmers for exposed toes or fingers that may extend outside the cast. The stockinettes for the hands and feet, as has been described, may be used in forming casts, splints and in forming thermoplastic or customized molded braces.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

I claim:

1. An orthopedic stockinette for use in the construction of a cast or splint for the hand, the stockinette comprising: a preformed sleeve of elastic fabric material that terminates in an end opening for allowing at least two fingers of the wearer to project through the opening and having two secondary sleeves for receiving individual fingers of the wearer, the secondary sleeves extending along the length of the received fingers; and
   an overlaying layer of hardenable cast material.
2. The orthopedic stockinette of claim 1, wherein:
   a portion of the sleeve is drawn together to form the secondary sleeves.
3. The orthopedic stockinette of claim 1, wherein:
   there is at least one side opening formed in the sleeve for receiving a thumb of the wearer.
4. The orthopedic stockinette of claim 1, wherein:
   the secondary sleeve projects beyond the end opening.
5. The orthopedic stockinette of claim 1, wherein:
   one of the secondary sleeves receives the thumb of the wearer.
6. The orthopedic stockinette of claim 1, wherein:
   the sleeve is configured so that the secondary sleeves receive one of the $2^{nd}$ and $3^{rd}$ fingers or the $4^{th}$ and $5^{th}$ fingers.
7. The orthopedic stockinette of claim 1, wherein:
   there are two side openings for alternately receiving the thumb of the wearer.
8. The orthopedic stockinette of claim 7, wherein:
   the sleeve is configured so that the secondary sleeves receive one of the $2^{nd}$ and $3^{rd}$ fingers or the $4^{th}$ and $5^{th}$ fingers, with the thumb being received within one of the two side openings and the remaining fingers projecting through the end opening.

9. An orthopedic cast or splint for the hand comprising: a stockinette of a preformed sleeve of elastic fabric material that terminates at one end in an opening for allowing at least two fingers of the wearer to project through the opening and at least one secondary sleeve for receiving an individual finger of the wearer, the secondary sleeve extending along the length of the received finger, and wherein there are two side openings for alternately receiving the thumb of the wearer; and
   an overlaying layer of hardenable cast material.
10. The orthopedic cast or splint of claim 9, wherein:
    the secondary sleeve receives the thumb of the wearer.
11. The orthopedic cast or splint of claim 9, wherein:
    the layer of hardenable cast material is formed from a unitary, preformed cast sleeve of flexible fabric material wherein at least a portion of the cast sleeve is impregnated with a hardenable material so that said portion of the sleeve is capable of substantially immobilizing an underlying body portion when the sleeve is positioned thereon, the preformed cast sleeve having at least one opening for receiving and conforming to at least one finger of the wearer.
12. The orthopedic cast or splint of claim 11, wherein:
    the at least a portion of the cast sleeve has a substantially uniform thickness that allows said portion to be cut with scissors without requiring a weakness zone.
13. The orthopedic cast or splint of claim 9, wherein:
    there are at least two secondary sleeves.
14. The orthopedic cast or splint of claim 13, wherein:
    there are only two secondary sleeves.
15. A method of forming a cast or splint, comprising:
    providing a stockinette of a preformed sleeve of elastic fabric material that terminates in an end opening for allowing at least two fingers of the wearer to project through the opening and having at least one secondary sleeve, and wherein there are two side openings for alternately receiving the thumb of the wearer;
    positioning the stockinette upon the hand of the wearer with at least two fingers of the wearer projecting through the opening and with the secondary sleeve receiving another individual finger of the wearer, the secondary sleeve extending along the length of the received finger; and
    applying a layer of hardenable cast material over the stockinette; and
    allowing the hardenable material to harden so that the selected body portion is substantially immobilized.
16. The method of claim 15, wherein:
    the sleeve is configured so that at least one secondary sleeves receives one of the $2^{nd}$ and $3^{rd}$ fingers or the $4^{th}$ and $5^{th}$ fingers, with the thumb being received within one of the two side openings and the remaining fingers projecting through the end opening.
17. The orthopedic cast or splint of claim 16, wherein:
    the sleeve is configured so that the secondary sleeves receive one of the $2^{nd}$ and $3^{rd}$ fingers or the $4^{th}$ and $5^{th}$ fingers.
18. The orthopedic cast or splint of claim 9, wherein:
    the sleeve is configured so that at least one secondary sleeve receives one of the $2^{nd}$ and $3^{rd}$ fingers or the $4^{th}$ and $5^{th}$ fingers, with the thumb being received within one of the two side openings and the remaining fingers projecting through the end opening.
19. The method of claim 15, wherein:
    there are at least two secondary sleeves.
20. The method of claim 19, wherein:
    there are only two secondary sleeves.

* * * * *